United States Patent
Schembri, Jr. et al.

(10) Patent No.: US 6,575,906 B1
(45) Date of Patent: Jun. 10, 2003

(54) RAPID-HEATING ULTRASOUND GEL WARMER

(75) Inventors: Frank M. Schembri, Jr., San Mateo, CA (US); Dermot P. McCartan, Sunnyvale, CA (US)

(73) Assignee: Acuson Corporation, Mountain View, CA (US)

( * ) Notice: Subject to any disclaimer, the term of this patent is extended or adjusted under 35 U.S.C. 154(b) by 77 days.

(21) Appl. No.: 09/839,614

(22) Filed: Apr. 19, 2001

(51) Int. Cl.⁷ .................................................. A61B 8/00
(52) U.S. Cl. ...................................................... 600/437
(58) Field of Search ................................. 600/459, 460, 600/437, 461, 462

(56) References Cited

U.S. PATENT DOCUMENTS

| | | | |
|---|---|---|---|
| 4,844,080 A | | 7/1989 | Frass et al. |
| 5,265,614 A | * | 11/1993 | Hayakawa et al. ......... 600/459 |
| 5,394,877 A | * | 3/1995 | Orr et al. .................... 600/459 |
| 5,490,038 A | * | 2/1996 | Scholder et al. .............. 174/50 |
| 5,568,810 A | | 10/1996 | Hamers et al. |

* cited by examiner

*Primary Examiner*—Francis J. Jaworski
*Assistant Examiner*—Maulin Patel

(57) ABSTRACT

An ultrasonic imaging system carries a holder that supports a gel container in an inverted position. The gel container includes a metallic cap including a heat exchanger in good thermal contact with the gel of the container, and the holder includes a heating element in good thermal contact with the cap. When the ultrasound system is powered, power is automatically applied to the heating element of the holder, thereby heating ultrasound coupling gel in the container near the spout.

16 Claims, 4 Drawing Sheets

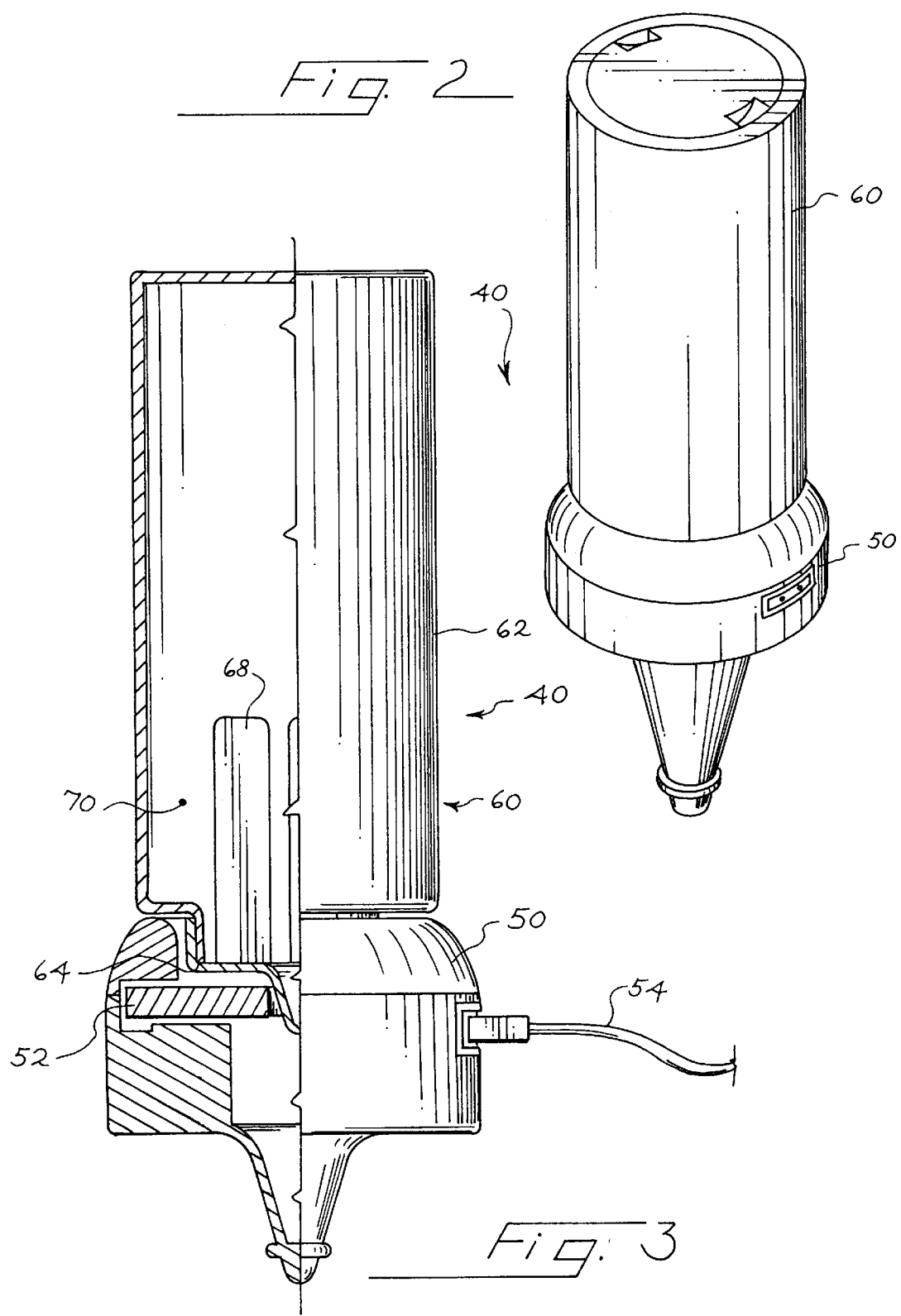

RAPID-HEATING ULTRASOUND GEL WARMER

BACKGROUND

The present invention relates to gel warmers used with ultrasonic imaging systems.

Generally, an ultrasound coupling gel is used with medical ultrasonic imaging probes to improve sonic coupling between the probe and the skin of the patient. Coupling gel is generally provided in a container, and the gel is preferably heated to near-body temperature before being applied to the skin of the patient.

One prior-art approach to this problem is to provide an enclosure into which one or more containers of ultrasound coupling gel are placed. The enclosure typically has a hinged cover, an electrical resistance heater, and a thermostat which connects to a common wall power outlet through a convenience plug. Gel within the containers is heated via conduction through the thermoplastic gel bottle. This results in a relatively long heating time that is required before the gel reaches body temperature. In addition, the enclosure-type heater is relatively large and expensive, and it must be controlled and powered independently of the ultrasound system.

Another prior-art approach is simply to place a container of ultrasound coupling gel on a warm surface of the ultrasound system. The surface may be heated by waste heat from the system monitor, electronics, or the like. This approach provides no automatic temperature control, and it often requires undesirably long heating times, if the gel is adequately heated at all. Because it relies on waste heat, it may not be appropriate for some ultrasound systems, such as those using flat-panel displays, or those in which waste heat is generated at a site remote from a convenient surface.

Thus, a need presently exists for an improved gel warmer for ultrasound coupling gel.

SUMMARY

By way of general introduction, the gel warmer described below in conjunction with the drawings includes a holder that is carried and powered by the ultrasound system and that is configured to hold a gel container in an inverted position. The holder includes a heating element, and the gel container includes a dispensing cap. This dispensing cap is in good thermal contact with the heating element when the gel container is inverted and placed in the holder. The dispensing cap includes a heat exchanger that is in good thermal contact both with the external contact surface of the cap and with the gel in the container near the spout.

Because the container is held in an inverted position, and because the heating element is in good thermal contact with gel in the vicinity of the spout, only a small heating time is required to bring an initial portion of the gel to the desired temperature.

The foregoing paragraphs have been provided by way of general introduction, and they should not be used to narrow the scope of the following claims.

BRIEF DESCRIPTION OF THE DRAWINGS

FIG. 2 is a perspective view of the gel warmer and the gel container of FIG. 1.

FIG. 3 is a cross-sectional/elevational view of the gel warmer and container of FIG. 2.

DETAILED DESCRIPTION OF THE PRESENTLY PREFERRED EMBODIMENTS

Figure 1:
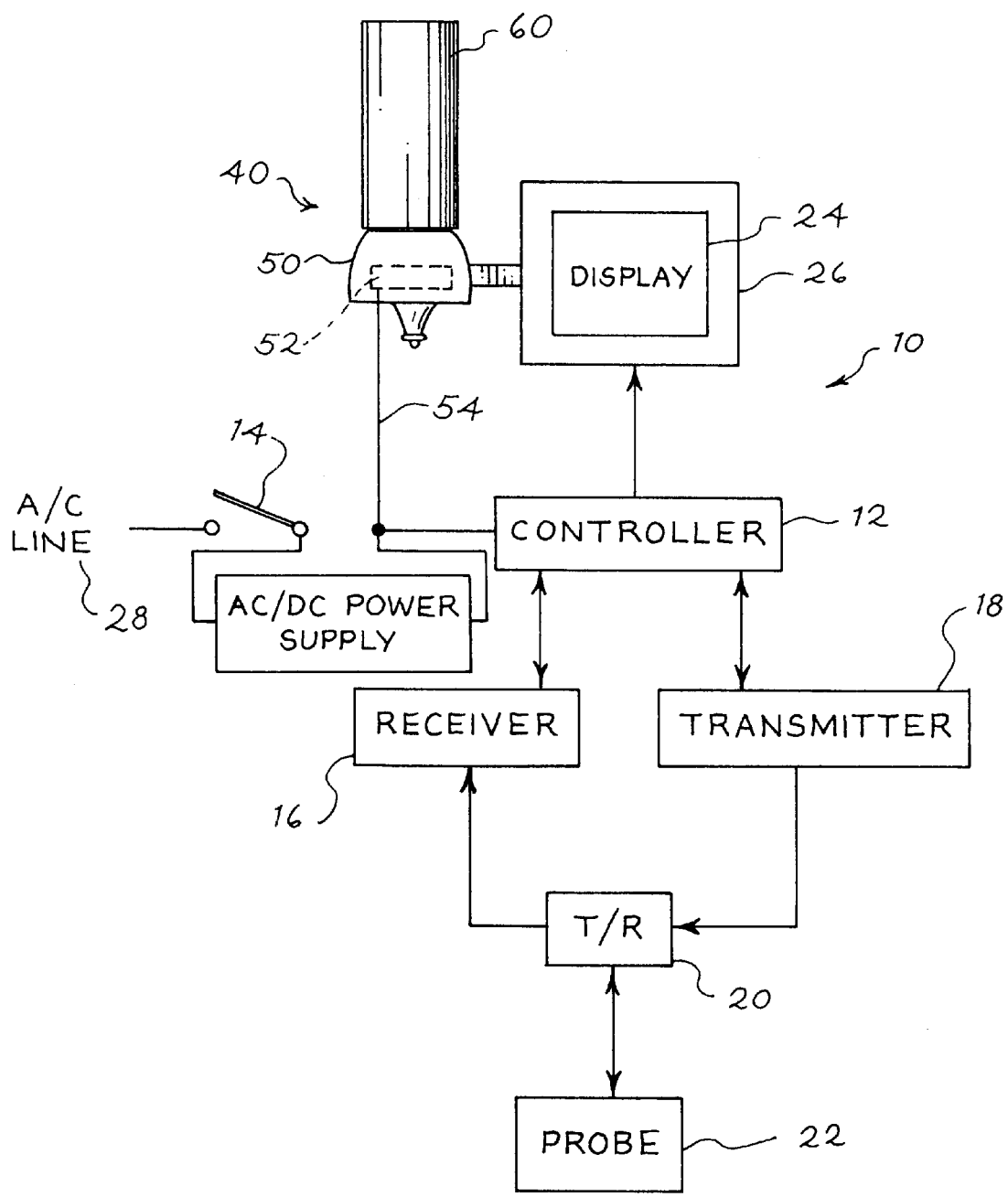
FIG. 1 is a block diagram of an ultrasonic imaging system that incorporates a preferred embodiment of this invention.

FIG. 1 is a block diagram of an ultrasonic imaging system 10 that incorporates a preferred embodiment of this invention. The imaging system 10 includes a controller 12 that is coupled via a power switch 14 with a voltage source 28 such as a wall outlet. The system 10 also includes a receiver 16 and a transmitter 18 coupled to the controller 12, and an ultrasound probe 22 coupled to the receiver 16 and the transmitter 18 by a transmit/receive switch 20. The controller 12 causes the transmitter 18 to apply transmit signals to one or more transducer elements included in the probe 20, which transmits ultrasonic waves in response thereto into the tissue being imaged. Ultrasonic reflections from the tissue are converted into electric receive signals by the probe 22 and applied to the receiver 16. These receive signals are then processed, and displayed on display 24 that is mounted in a housing 26.

The foregoing elements 10–28 can be conventional, and it is not intended to limit this invention to any particular type of ultrasonic imaging system, receiver, transmitter, probe or the like. Instead, this invention can be adapted for use with the widest variety of ultrasonic imaging systems.

As shown schematically in FIG. 1, the system 10 also includes an ultrasound gel warmer 40 including a holder 50 that is carried by the housing 26 in a position convenient to the system operator. The holder 50 includes a heater 52 that includes a resistive heater powered by voltage supplied by a power cable 54. This power cable 54 is connected to the power switch 14 such that when the ultrasonic imaging system 10 is powered, the heater 52 is automatically powered as well. If desired, an optional switch (not shown) can be provided to allow the system operator to turn the heater 52 off, though in normal usage it will often be desirable to leave the switch (if present) closed, such that the heater 52 is automatically powered whenever the system 10 is powered.

Figure 4:
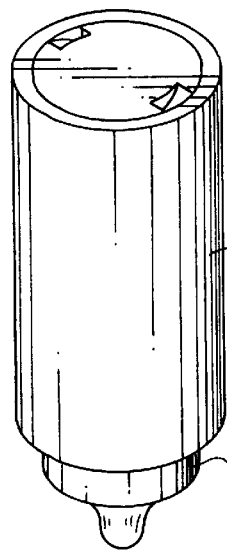
FIG. 4 is a perspective view of the gel container of FIG. 3.
Figure 5:
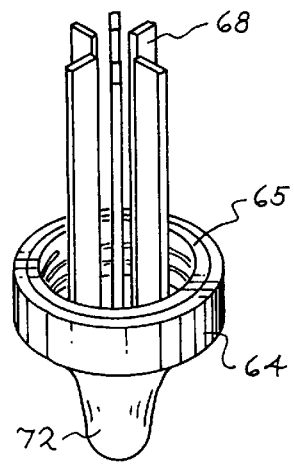
FIGS. 5 and 6 are two perspective views of the dispensing cap included in the container of FIG. 4.
Figure 6:
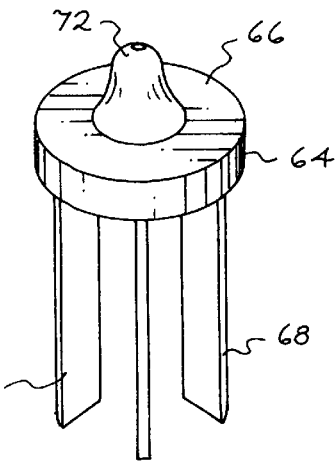

The gel warmer 40 structurally includes two main elements: the holder 50 described above and the gel container 60. FIGS. 2 and 3 provide overall views showing the interrelationship of the gel container 60 when inverted and held in place by the holder 50. FIG. 4 shows an inverted perspective view of the gel container 60 removed from the holder 50. As shown in FIG. 4, the gel container 60 includes a body 62 and a cap 64. The body 62 may be a conventional thermoplastic container of the type commonly used to supply ultrasound coupling gel. The cap 64 is threaded onto the body 62, and FIGS. 5 and 6 show two views of the cap 64 removed from the body 62. As shown in FIG. 6, the cap 64 includes a spout 72 that is surrounded by an external heat contact surface 66. As best shown in FIG. 5, the cap 64 includes an array of protruding elements 68 in good thermal contact with the gel 70 (FIG. 3) in the container 60 near the spout 72. In the illustrated example, the protruding elements 68 are formed as fins, though many other shapes are possible. For example, the protruding elements 68 may be formed as coils, plates, tubes or other shapes designed to provide adequate surface area while providing acceptable resistance to flow of gel out of the container 60.

The cap 64 seals the body 62 of the container 60 and provides efficient thermal coupling between the heater 52 and the ultrasound gel 70. The cap 64 is designed to provide large-area contact with the gel 70 and with the heater 52 with minimum thermal mass. Preferably, the cap 64 is formed from a material with high thermal conductivity such as an aluminum alloy or copper. By way of example, the cap 64 can be formed by conventional casting or stamping and brazing techniques.

The example shown in FIGS. 5 and 6 can be cast of aluminum alloy or copper. Die casting, investment casting or other common metal casting methods can be used as appropriate for the application. In this example, the one-piece, cast part includes the protruding elements 68, the spout 72, and the external contact surface 66. The body sealing threads 65 can either be incorporated into the metal casting, or produced in a secondary operation by overmolding a thermoplastic thread ring onto the metal cap 64.

Depending upon the base material selected, the cap 64 can be finished in any suitable manner to provide corrosion protection. For example, when the cap 64 is formed of an aluminum alloy, chemical conversion coating, anodizing, or electroplating can be used. Similarly, electroplating is well suited for finishing the cap 64 when made of copper.

When the cap 64 is made of stamped and brazed elements, the cap 64 can be made of thin sheet material (again copper or aluminum alloy) produced by deep-drawing, metal-spinning, impact-extruding, or other metal-forming processes. The protruding elements 68 can be produced by a separate metal forming process such as by sawing, stamping, extruding or casting processes. The protruding elements 68 are brazed, soldered or otherwise bonded to the cap 64 to form an integrated assembly, and the assembled parts can be plated if desired. Stamping techniques allow greater control over the thinness of the material used for the protruding elements 68 and a wider range of materials and geometries.

By way of one non-limiting example, the protruding elements 64 can be 2 inches in length, 0.35 inches in width, and 0.06 inches in thickness, and the body of the cap 64 can be 0.06 inches in thickness with a outside diameter of 1.75 inches. The cap 64 in this example is formed of aluminum alloy 2011 and is black anodized.

Figure 7:
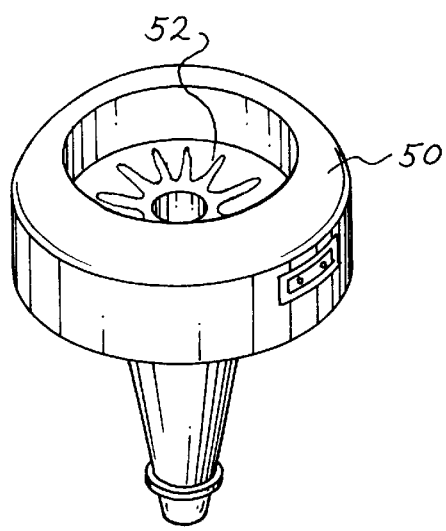
FIG. 7 is a perspective view of the holder of FIG. 2 with the gel container removed.
Figure 8:
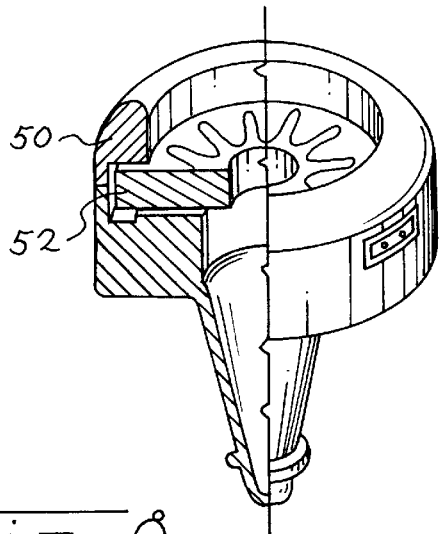
FIG. 8 is a partial sectional view of the holder of FIG. 7.

FIGS. 7 and 8 provide further views of the holder 50, which holds the gel container 60 in an inverted position with the external contact surface 66 of the cap 64 of the gel container 60 in large-area thermal contact with the heater 52. In this example, the heater 52 is fixedly mounted in place in the holder 50. The holder 50 and the cap 64 are designed as a unit in such a way as to only allow the gel container 60 to be installed into the holder 50 in the correct, inverted orientation. The holder 50 also retains the gel container 60 while the ultrasound system is moved, while still allowing for easy insertion and extraction of the gel container 60 from the holder 50.

The holder 50 can for example be formed from molded thermoplastic materials for ease of construction and low manufacturing costs. Of course, other process and materials can be used, depending upon the application.

Figure 9:
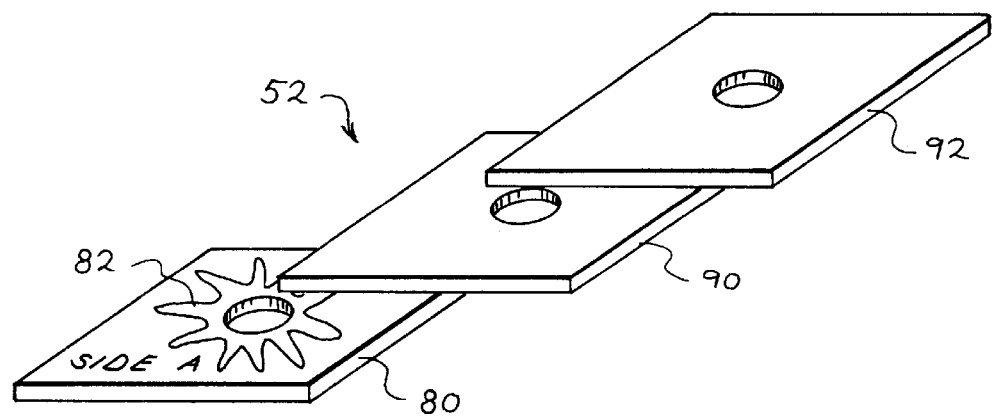
FIG. 9 is an exploded perspective view of the heater included in the holder of FIG. 7. RAPID-HEATING ULTRASOUND GEL WARMER
Figure 10:
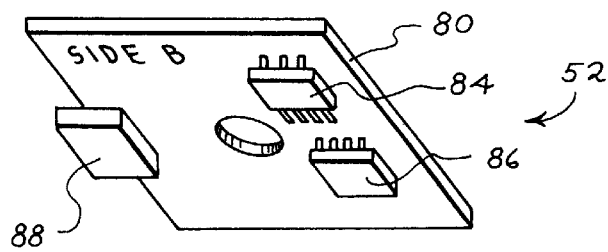
FIG. 10 is a bottom perspective view of the heater of FIG. 9.
Figure 11:
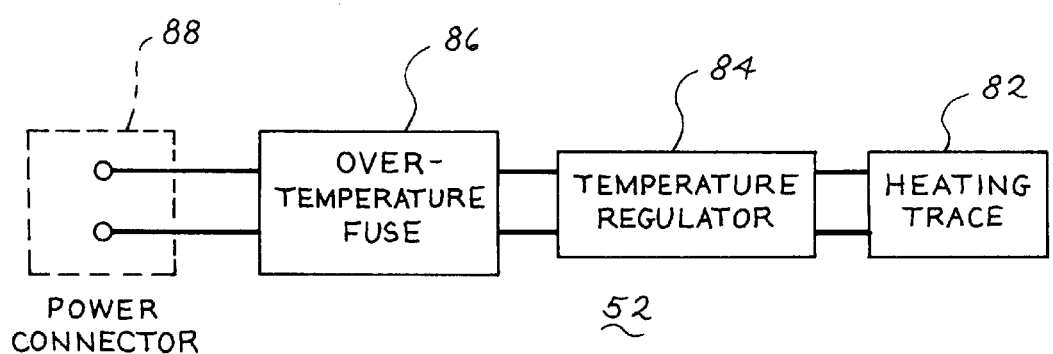
FIG. 11 is a schematic diagram showing how the elements of FIG. 10 are electrically connected.

FIGS. 9, 10 and 11 provide further information regarding the heater 52. In this example, the heater 52 includes a resistive heating element such as resistive traces 82 on an upper side of a substrate such as a printed circuit board 80. For example, these traces 82 can be formed as flat copper foil traces etched onto the top, copper-clad surface of a common printed circuit board laminate material such as FR4. The geometry and length of the traces 82 is designed to provide for a suitable power dissipation at the design voltage. The thermal power used to heat the gel is generated via resistive heating of the traces 82. The top surfaces of the traces 82 are electrically insulated by an insulator 90 from contact with the contact surface 66 of the cap 64. This electrical insulation 90 is preferably thin, and it serves to prevent the traces 82 from shorting together when the metallic cap 64 is placed in the holder 50, while allowing effective heat transfer from the traces 82 to the cap 64 and the gel 70. Organic coatings such as a solder mask or thin dielectric films such as Kapton™ or Teflon™ can be used for the insulator 90. Films such as this provide the required electrical insulation while providing good wear and abrasion resistance at low cost. While such films are characterized by relatively poor heat conductivity, the film thickness is preferably minimized to reduce the thermal insulation provided by the insulator 90. For example, an insulator thickness of 1 to 3 thousandths of an inch may be suitable. Organic coatings such as solder mask are even less expensive but are somewhat lower in abrasion resistance. A thin metal plate 92 can optionally be placed over the insulator 90 to improve abrasion resistance.

As shown in FIG. 10, the bottom side of the printed circuit board 80 carries a temperature controller 84, an over-temperature fuse 86, and a power connector 88. Appropriate electrical wiring is etched onto the bottom side copper clad surface of the printed circuit board laminate. In this manner, the resistive heating traces 82, and the associated temperature control circuitry can be manufactured economically using standard printed circuit board manufacturing materials, equipment and processes in a single operation. Optimally, the temperature controller 84 includes a single integrated circuit that includes temperature measurement circuitry and control circuitry in a single package. The controller 84 senses the temperature, compares it with a desired setting, and cycles electrical power on and off to the resistive traces 82 to maintain the temperature within a desired range. For safety, the over-temperature fuse 86 operates as a resettable or non-resettable thermal circuit breaker installed in series with the power connector 88, thus providing for redundant control, and preventing overheating in the event of a failure of the temperature controller 84. FIG. 11 shows a schematic diagram of the manner in which the electrical power from the power connector 88 is passed in series through the over-temperature fuse 86 and the temperature controller 84 to the heating trace 82.

As an alternative construction for the heater 52, a commercially available resistance heater can be bonded to a thin metal plate. With this construction, the required control electronics are mounted separately on a secondary printed circuit board, and an electrical cable joins the two parts together. This design yields similar operation as that described above, but it requires additional components and assembly that increase cost.

In order to improve safety, the heating traces 82 or other heating element preferably operates at a low voltage such as 12 volts, and are electrically isolated from the AC line. The heating element can also be implemented as a flexible film heater (either wire-wound or photochemically machined), a heater cartridge, a resistor, or a heat dissipating semiconductor device, or the like. If desired, the heater 52 can include a high-thermal-conductivity, low-thermal-mass contact plate positioned to contact the cap 64.

Other alternatives include separate switching relay, transistor, triac, mosfet, etc. controlled by the controller. Also, the temperature controller 84 can provide gradually modulated heater current to provide rapid warm-up without exceeding the temperature set-point. For example, pulse width modulation techniques or on-off control with hysteresis can be used.

OPERATION

In use, the original cap of the gel container 60 is removed and discarded, if the cap 64 was not originally supplied pre-installed. Then the cap 64 is then screwed in place on the body 62. The gel container 60 is then inverted and placed in the holder 50, with the exterior contact surface 66 in good thermal contact with the heater 52. Because the gel container 60 is inverted, gel is positioned in contact with the cap 64, even in a partially filled container. In this example, the exterior contact surface 66 and the heater 52 both extend substantially around the spout 72.

When the system operator closes the power switch 14 of the system 10, the heater 52 is automatically switched on, thereby warming a volume of gel required for at least the first patient application in a few minutes. The low thermal mass of the cap 64 reduces warm-up time and helps insure that heat generated by the heater 52 is transmitted rapidly to the gel 70. The system operator then removes the gel container 60 from the holder 50 and applies the gel 70 in the usual way, before returning the gel container 60 to the holder 50 to continue gel heating. The gel is readily dispensed without the need to shake the container, because the container is held in the inverted position with the spout below the body of the container.

The gel warmer described above provides the advantage that it heats the gel needed for an initial application very rapidly, substantially eliminating set-up time prior to an ultrasound examination. This is an important advantage, especially for mobile or portable ultrasound systems. Since the gel warmer is integrated into the ultrasound system, the system operator is not required to control the gel warmer separately. Also, the gel warmer is simple, automatic in operation, and low in cost.

Many alternatives are possible. For example, the heating traces 82 may be integrated with the cap 64 and powered by a low-voltage connection between the cap 64 and the holder 50. This method of construction further reduces warm-up time by eliminating any temperature drop across a thermal contact surface, at the expense of a more complicated cap and electrical connections.

The foregoing detailed description has described only a few of the many forms that this invention can take. This detailed description is therefore intended by way of illustration and not limitation. It is only the following claims, including all equivalents, that are intended to define the scope of this invention.

What is claimed is:

1. In an ultrasound imaging system the improvement comprising:
    a gel container comprising a body and a dispenser carried by the body;
    a gel container holder carried by the imaging system, said container holder configured to hold the container in an inverted orientation with the dispenser below the body;
    a heating element included in one of the gel container and the holder;
    a voltage source included in the imaging system;
    said voltage source connected to the heating element at least when the container is positioned in the container holder.

2. In an ultrasound imaging system the improvement comprising:
    a gel container comprising a body and a dispenser carried by the body;
    a gel container holder carried by the imaging system, said container holder configured to hold the container in an inverted orientation with the dispenser below the body; and
    a heating element included in the container holder and thermally coupled with the dispenser when the container is positioned in the holder.

3. The invention of claim 1 or 2 wherein the dispenser comprises a heat exchanger in thermal contact with a gel contained in the container and in thermal contact with the heating element at least when the container is positioned in the holder.

4. The invention of claim 1 or 2 wherein the dispenser comprises a gel-dispensing cap.

5. The invention of claim 4 wherein the cap comprises:
    a thermally conductive external contact surface; and
    a set of protruding elements in good thermal contact (1) with the external contact surface and (2) with a gel contained in the container.

6. The invention of claim 5 wherein the heating element is in good thermal contact with the external contact surface when the container is positioned in the holder.

7. The invention of claim 6 wherein the cap comprises a spout, wherein the exterior contact surface extends at least partially around the spout, and wherein the heating element extends at least partially around the spout when the container is positioned in the holder.

8. The invention of claim 2 wherein the dispenser comprises a spout, and wherein the heating element extends at least partially around the spout when the container is positioned in the holder.

9. The invention of claim 1 or 2 further comprising:
    a temperature controller coupled with the heating element.

10. The invention of claim 9 further comprising a substrate, wherein the heating element is carried by a first side of the substrate, and wherein the temperature controller is carried by a second side of the substrate, opposite the first side.

11. The invention of claim 10 wherein the substrate comprises a printed circuit board.

12. The invention of claim 10 further comprising an over-temperature fuse carried by the substrate and coupled with the temperature controller.

13. An ultrasonic imaging system comprising:
    an ultrasonic transmitter,
    an ultrasonic receiver,
    a controller coupled with the transmitter and the receiver;
    a power switch operative to selectively apply power to the controller; and
    a gel warmer coupled with the power switch such that the gel warmer is automatically activated when the power switch powers the controller.

14. The invention of claim 13 further comprising:
    a housing;
    a display coupled with the receiver and carried by the housing;
    wherein the gel warmer is carried by the housing.

15. The invention of claim 14 wherein the gel warmer comprises a gel container holder configured to hold a gel container in an inverted position.

16. The invention of claim 15 wherein the gel warmer is included in the gel container holder.

* * * * *